US006387631B1

(12) United States Patent
Arnold et al.

(10) Patent No.: US 6,387,631 B1
(45) Date of Patent: *May 14, 2002

(54) POLYMER COATED SURFACES FOR MICROARRAY APPLICATIONS

(75) Inventors: Lyle J. Arnold, Poway, CA (US); Samuel P. Sawan, Tyngsborough, MA (US); Paul H. Lee, Pleasanton, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/775,319

(22) Filed: Feb. 1, 2001

Related U.S. Application Data

(63) Continuation of application No. 09/532,419, filed on Mar. 22, 2000.

(51) Int. Cl.[7] .......................... C12Q 1/68; C12N 15/11; C07K 16/00; C07K 2/00; C12M 1/36
(52) U.S. Cl. ................ 435/6; 435/7.1; 435/4; 435/287.2; 435/287.9; 435/288.3; 422/68.1; 536/23.1; 530/300; 530/387.1; 530/388.1
(58) Field of Search .................. 435/6, 68.1, 287.2, 435/287.9, 288.3, 7.1, 4; 536/23.1; 530/300, 387.1, 388.1

(56) References Cited

U.S. PATENT DOCUMENTS

| 5,266,471 A | * 11/1993 | Schmitt ....................... 435/178 |
| 5,474,895 A | 12/1995 | Ishii et al. ....................... 435/6 |
| 5,514,785 A | 5/1996 | Van Ness et al. .......... 536/22.1 |
| 5,667,976 A | * 9/1997 | Van Ness et al. ............... 435/6 |
| 5,690,894 A | * 11/1997 | Pinkel et al. ............... 422/68.1 |
| 5,919,523 A | 7/1999 | Sunderberg et al. ........ 427/333 |
| 6,013,789 A | 1/2000 | Rampal ...................... 536/25.3 |

FOREIGN PATENT DOCUMENTS

EP     0947246 A     10/1999

OTHER PUBLICATIONS

Ferguson et al. "A fiber–optic DNA biosensor microarray for the analysis of gene expression" Nature Biotechnology, Dec. 1996, 14: 1681–1684.*
Beattie et al. "Hybridization of DNA targets to glass–tethered oligonucleotide probes" Molecular Biotechnology, 1995, 4: 213–225.*
Academic Press Dictionary of Science and Technology, Academic Press, 1992, p. 821.*
Chrisey, L.A. et al., "Covalent attachment of synthetic DNA to self–assembled monolayer films", Nuc. Acids Res., 24(15): 3031–3039 (1996).
Cohen, G. et al., "Convalent attachment of DNA oligonucleotides to glass", Nuc. Acids Res., 25(4): 911–912 (1997).
Beier, M. and J.D. Hoheisel, "Versatile derivatisation of solid support media for convalent bonding on DNA–microchips", Nuc. Acids Res., 27 (9): 1970–1977 (1999).

(List continued on next page.)

Primary Examiner—W. Gary Jones
Assistant Examiner—B J Forman
(74) Attorney, Agent, or Firm—Richard Aron Osman (57) ABSTRACT

Methods are provide for modifying a solid support, such as a glass slide, by silylating with an agent having the formula $H_2N-(CH_2)_n-SiX_3$ where n is between 1 and 10, and X is independently chosen from OMe, OEt, Cl, Br, or I, then activating with a crosslinking reagent, followed by reacting with an amine-containing polymer. The support can optionally be reacted with a crosslinking reagent again. The support thus modified may be used to make arrays and microarrays where a plurality of targets are stably associated with the support and arranged in a defined manner.

34 Claims, 3 Drawing Sheets

OTHER PUBLICATIONS

Rogers, Y. et al., "Immobilization of Oligonucleotides onto a Glass Support via Disulfide Bonds: A Method for Preparation of DNA Microarrays", *Analytical Biochem.*, 266: 23–30 (1999).

Joos, B. et al, "Convalent Attachment of Hybridizable Oligonucleotides to Glass Supports", *Analytical Biochem.*, 247: 96–101 (1997).

Chan, V. et al., "The Biophysics of DNA Hybridization with Immobilized Oligonucleotide Probes", *Biophys. J.*, 69: 2243–2255 (1995).

Southern, E. et al., "Molecular interactions on microarrays", *Nature Genet. Supp.*, 21: 5–9 (1999)..

Beattie, W.G. et al., "Hybridization of DNA Targets to Glass–Tethered Oligonucleotide Probes", *Molecular Biotech.*, 4: 213–225 (1995).

Beattie, K.L. et al., "Advances in Genosensor Research", *Clin. Chem.*, 41(5): 700–706 (1995).

Guo, Z. et al., "Direct fluorescence analysis of genetic polymorphisms by hybridization with oligonucleotide arrays on glass supports", *Nuc. Acids Res.*, 22 (24): 5456–5465 (1994).

Maskos, U. and E.M. Southern, "Oligonucleotide hybridisations on glass supports: a novel linker for oligonucleotide synthesis and hybridisation properties of oligonucleotides synthesised in situ", *Nuc. Acids Res.*, 20 (7): 1679–1684 (1992).

Befani O. et al. Oct. 1998, Biotechnology and Applied Biochemistry, Academic Press, US, 28(2):99–104.

* cited by examiner

FIGURE 1.

| F23S1 | 5'-ATCCGCCACATAAGATGCACAAAATGAGCCTAT AACATTGAATTTTATGATAGAACGAA-3' | Seq. ID. No. 1 |
|---|---|---|
| F23S200 | 5'-AACATATGCGAGTTATTGAACTTGGTAGAAAGT ACGGAAAGACACAATAGTATTATCAA-3' | Seq. ID. No. 2 |
| F23S431 | 5'-AAGTCACAATATCTTATTATTATTTGGAAGCTTT TATATGCATCTAATGGTCATAAATC-3' | Seq. ID. No. 3 |
| F23S805 | 5'-AAGTTTCATTAGTGACATTAAAAGAAGAAAACT GATGTTTTGAAATGTGTTAAGCAAAG-3' | Seq. ID. No. 4 |
| F23S846 | 5'-AATGATTAAGACAATCTCAAGCTGCTCTAAGCAG TATCTTCGACAGCTTGCTCTGCTTC-3' | Seq. ID. No. 5 |

| F44S74 | 5'AGACGATAAAATCACAGCCCTATAATTTATGCAA CAGTGTTTGCTTCTAAATCAACGTG-3' | Seq. ID. No. 6 |
|---|---|---|
| F44S218 | 5'GAAGAAGAGAAGAACATAAGCCTTCTCATTCAG AACATGTAAATAGTGGCTAAATGGT-3' | Seq. ID. No. 7 |
| F44S668 | 5'TAAAGCCTACTTACGAGAAGAGAGGTAGGACGTT GAAGCCACATCCATAAATAATTTTT-3' | Seq. ID. No. 8 |
| F44S781 | 5'CAGTCAGTAACCTTTTAGGCATTGATTCTAGTAA CTGTCGAACATTATTAACCTTGATG-3' | Seq. ID. No. 9 |
| F44S943 | 5'CTTTTGGTAGTATAGGGGAAAACTCAGCTTGAAA CTTTTCGTAATTGAGTAGGCCAAGT-3' | Seq. ID. No. 10 |

SEQUENCE LISTING

```
<160> NUMBER OF SEQ ID NOS: 10

<210> SEQ ID NO 1
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S1

<400> SEQUENCE: 1
atccgccaca taagatgcac aaaatgagcc tataacattg aattttatga t agaacgaa      59

<210> SEQ ID NO 2
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S200

<400> SEQUENCE: 2
aacatatgcg agttattgaa cttggtagaa agtacggaaa gacacaatag t attatcaa     59

<210> SEQ ID NO 3
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S431

<400> SEQUENCE: 3
aagtcacaat atcttattat tatttggaag cttttatatg catctaatgg t cataaatc     59

<210> SEQ ID NO 4
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S805

<400> SEQUENCE: 4
aagtttcatt agtgacatta aaagaagaaa actgatgttt tgaaatgtgt t aagcaaag     59
```

```
<210> SEQ ID NO 5
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S846

<400> SEQUENCE: 5
aatgattaag acaatctcaa gctgctctaa gcagtatctt cgacagcttg c tctgcttc      59

<210> SEQ ID NO 6
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F44S74

<400> SEQUENCE: 6
agacgataaa atcacagccc tataatttat gcaacagtgt ttgcttctaa a tcaacgtg      59

<210> SEQ ID NO 7
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F44S218

<400> SEQUENCE: 7
gaagaagaga agaacataag ccttctcatt cagaacatgt aaatagtggc t aaaatggt      59

<210> SEQ ID NO 8
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F44S668

<400> SEQUENCE: 8
taaagcctac ttacgagaag agaggtagga cgttgaagcc acatccataa a taattttt      59

<210> SEQ ID NO 9
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F44S781

<400> SEQUENCE: 9
cagtcagtaa cctttaggc attgattcta gtaactgtcg aacattatta a ccttgatg       59

<210> SEQ ID NO 10
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F44S943

<400> SEQUENCE: 10
cttttggtag tatagggaa aactcagctt gaaacttttc gtaattgagt a ggccaagt       59
```

POLYMER COATED SURFACES FOR MICROARRAY APPLICATIONS

This application is a Continuation of application Ser. No. 09/532,419, filed Mar. 22, 2000.

FIELD OF INVENTION

The present invention relates generally to the field of arrays and microarrays and, more particularly, to compositions and methods for modifying the solid supports of the arrays and microarrays.

BACKGROUND OF THE INVENTION

Microarrays having a plurality of polymeric molecules spatially distributed over and stably associated with the surface of a solid support are becoming an increasingly important tool in bioanalysis and related fields. Microarrays of both polypeptides and polynucleotides have been developed and find use in a variety of applications, such as gene sequencing, monitoring gene expression, gene mapping, bacterial identification, drug discovery, and combinatorial chemistry. One area in particular in which microarrays find use is in gene expression analysis.

The current methods of manufacturing arrays and microarrays immobilize the polynucleotides at specific sites on solid supports by either synthesizing the polynucleotides at the desired position, or by presynthesizing the polynucleotides and then attaching them to the solid support. U.S. Pat. No. 5,445,934 discloses a method of on-chip synthesis. In this process, a glass slide is derivatized with a chemical species containing a photocleavable protecting group. Selected sites are deprotected by irradiation through a mask. The deprotected sites are then reacted with a DNA monomer containing a photoprotective group. The process of masking, deprotecting, and reacting is repeated for each monomer attached until an array of site-specific polynucleotide sequences is achieved.

Methods for immobilizing pre-synthesized polynucleotides onto solid supports include simple adsorption, ultra violet linking, and covalent attachment. In general, the attachment of unmodified polynucleotides to unmodified solid supports is inefficient. Therefore, the polynucleotides or the solid support has to be modified to enable attachment. Thus, polynucleotides modified with bovine serum albumin adsorb passively to microtiter plates (Southern, E. M. PCT 89/00460), and biotinylated polynucleotides bind tightly to plates or beads that are coated with avidin or streptavidin. In another method, Carrico, et al., U.S. Pat. No. 4,806,546, have described treatment of a nylon support with an alkylating agent to introduce amidine groups onto the surface of the nylon. The derived nylon surface possesses the capacity to noncovalently bind single stranded nucleic acids. The noncovalently bound nucleic acids are then used as probes to detect specific target nucleic acids in solution.

In a different approach, the solid support is modified with a suitable functional group and/or linker. Thus, the solid support is modified to carry an active group, such as hydroxyl, carboxyl, amine, aldehyde, hydrazine, epoxide, bromoacetyl, maleimide, and thiol groups (Lund et al., U.S. Pat. No. 5,474,895) on its surface to which oligonucleotide can be covalently or non-covalently linked. For example, U.S. Pat. No. 5,514,785 to Ness et al. discloses a process for covalently attaching an oligonucleotide to a nylon support. The nylon support is first treated with an amine-containing polymer thereby forming a reactive imidate ester on the surface of the nylon support. The imidate esters on the surface are then reacted with a primary or secondary amine-containing polymer to form amidine residues that are then conjugated with activated polynucleotides. In another method, disclosed in U.S. Pat. No. 6,013,789 to Rampal, polypropylene film is first aminated by a plasma discharge in the presence of ammonia gas, and then contacted with an oligonucleotide having a terminal phosphorimidazolide, whereupon the oligonucleotide becomes covalently linked to the polypropylene film via a phosphoramidate bond.

The immobilized polynucleotides can be used to construct arrays or microarrays for hybridization assays. A typical method of using microarrays involves contacting nucleotide sequences contained in a fluid with the sequences immobilized on the microarrays under hybridization conditions, and then detecting the hybridization complex. The resultant pattern of hybridized nucleic acids provides information regarding the profile of the nucleotide constituents in the sample tested. A widely used method for detecting the hybridization complex in microarrays is by fluorescence. In one method, probes derived from a biological sample are amplified in the presence of nucleotides that have been coupled to a fluorescent label (reporter) molecule so as to create labeled probes, and the labeled probes are then incubated with the microarray so that the probe sequences hybridize to the complementary sequences immobilized on the microarray. A scanner is then used to determine the levels and patterns of fluorescence.

The art methods of immobilizing polynucleotides on solid support usually result in low coupling yields. In addition, the polynucleotides are bound on the flat two-dimensional surface of the substrate, whereas it is thought that binding the polynucleotides within a three-dimensional polymer matrix would enable more efficient hybridization. Thus, there exists a need for methods and procedures for immobilizing polynucleotides to solid support for fabricating arrays and microarrays.

SUMMARY OF THE INVENTION

Methods are provided for modifying a solid support by silylating the support with an agent having the formula $H_2N—(CH_2)_n—SiX_3$ where n is between 1 and 10, and X is independently chosen from OMe, OEt, OPr, Cl, Br, or I, then activating with a crosslinking reagent, followed by reacting with an amine-containing polymer. The support can be further treated with a cross-linking reagent. A plurality of targets may be stably associated with the support and arranged in a defined manner.

Also provided are methods of attaching targets to a solid support. The support is silylating with an agent having the formula $H_2N—(CH_2)_n—SiX_3$ where n is between 1 and 10, and X is independently chosen from OMe, OEt, Cl, Br, or I, then activating with a crosslinking reagent, followed by reacting with an amine-containing polymer. The support can be further treated with a crosslinking reagent. The support is then contacted with the targets that can optionally have a spacer arm at the 5'-end or the 3'-end of the target.

Also provided is an array of polynucleotides made by modifying a glass slide by silylating with an agent having the formula $H_2N—(CH_2)_n—SiX_3$ where n is between 1 and 10, and X is independently chosen from OMe, OEt, Cl, Br, or I, then activating with a crosslinking reagent, followed by reacting with an amine-containing polymer. The support can optionally be reacted with crosslinking agent. A plurality of polynucleotides are stably associated with the support in a defined manner.

These and other objectives, advantages, and features of the invention will become apparent to those persons skilled

DETAILED DESCRIPTION

Before the present methods, arrays and microarrays are described, it is to be understood that this invention is not limited to particular methods and arrays described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

DEFINITIONS

It must be noted that, as used in the specification and the appended claims, the singular forms "a," "an" and "the" include plural referents unless the context clearly dictates otherwise. Thus, for example, reference to "a probe" means that more than one such probe can be present in the composition. Similarly, reference to "a microarray element" or "the microarray element" includes the possibility of one or more microarray elements, and the like.

The term "solid support" refers to any surface onto which targets, such as nucleic acids, may be immobilized for conducting assays and reactions.

The term "target", "DNA element" or "microarray element" refers to a molecule that has an affinity for a given sample. Targets may be naturally occurring or synthetic molecules, and may be attached, covalently or noncovalently, to a surface, either directly or via a specific binding substance. Examples of targets which can be employed by this invention include, but are not restricted to, DNA, RNA, oligonucleotides, oligosaccharides, polysaccharides, sugars, proteins, peptides, PNAs, monoclonal antibodies, toxins, viral epitopes, hormnones, hormone receptors, enzymes, enzyme substrates, cofactors, and drugs including agonists and antagonists for cell surface receptors.

The term "microarray" refers to an array of targets synthesized or attached or deposited on a substrate, such as paper, nylon or other type of membrane, filter, chip, glass slide, beads, or any other suitable solid support, at high density.

In one embodiment, polynucleotides and activated polynucleotides are attached to an amine treated solid support, such as a glass slide. The attachment can be covalent, non-covalent, or a combination of the two. The array or the microarray thus manufactured may be contacted, under hybridization conditions, with a fluid sample containing labeled nucleic acid probes complementary to the polynucleotide target. The hybridization pattern from the probe may be detected to obtain information about the genetic profile of the labeled nucleic acid sample.

In general, the invention comprises the steps of treating a solid support with a silylating agent to give aminoalkylsilated solid support; reacting the treated solid support with a crosslinking reagent, preferably the multifunctional reagent, cyanuric chloride (i.e., 2,4,6-trichlorotriazine), followed by treatment with an amine-containing polymer, preferably polyethylenimine (PEI); optionally activating the PEI-modified surface with a crosslinking reagent; and then contacting the solid support with targets, such as polynucleotides that may be optionally modified to contain a linker group.

In the present invention, a solid support is treated initially with a silylating agent. The solid support may be composed of any material that is compatible with the fluids with which the surface comes in contact, such as, for example, glass, gel, silicon, fused silica, plastic, ceramic, paper, metal, or other polymers such as nylon. The substrate may be rigid or flexible, and may define a shape that is substantially planar in the shape of a circle, an ellipse, a square, a rectangle, a triangle, or any other convenient substantially planar shape. In the preferred embodiment, a rectangular glass slide is used as the substrate. The silylating agents are chosen such that they react with the reactive groups present at the surface of the substrate to form a primary amine. For example, the silylating agent $NR'_2$—R—$SiX_3$, where R' is independently chosen from hydrogen, methyl, ethyl, or propyl, R is $(CH_2)_n$, where n is 1 to 10, and X is independently chosen from hydrogen, alkyl, Oalkyl, F, Cl, Br, or 1, where alkyl is preferably loweralkyl of from 1 to 6 carbon atoms with the proviso that all three X groups together cannot be alkyl, upon reaction with the Si—OH groups present at or near the surface of the glass slide yields aminoalkysilanated glass slides. In the preferred embodiment, the rectangular glass slide is reacted with 3-aminopropyl-trimethoxysilane to yield aminopropylsilanated glass slides.

The aminoalkylsilanated glass slide may be treated with a multifunctional crosslinking reagent. In one embodiment, the crosslinking reagent contains a reactive group at one end that can react with the nitrogen atom of an amine group to form a nitrogen-carbon bond. Such reactive groups are well known in the art, and include halides, esters, epoxides, and the like. The crosslinking agent additionally contains a protected reactive group at the opposite end that is capable of being deprotected and undergoing further reaction with the amine-containing polymer. Crosslinking reagents include, but are not limited to, N-succinimidyl-4-(iodoacetamido)-benzoate (SIAB), disuccinimidyl suberate, 1-ethyl-3-(dimethylaminopropyl)carbodiimide and 2,4,6-trichlorotriazine (cyanuric chloride). The crosslinking reagent is preferably cyanuric chloride.

The aminoalkylsilanated substrate treated with the crosslinking reagent may then be reacted with an amine-containing polymer. Any primary, secondary, or tertiary amine-containing polymer may be employed. The amine-containing polymer may be polyethylenimine, polyallylamine, polyvinylamine, polyhistidine, polyormithine, polylysine, and polyarginine. In the preferred embodiment, the solid substrate, having been silylated and activated with the crosslinking reagent, is coated and modified with polyethylenimine (PEI). The resulting PEI-modified surface of the solid surface may optionally be treated with a crosslinking reagent again, such as cyanuric chloride.

The PEI-coated glass slides may be used for manufacturing arrays and microarrays. In the preferred embodiment, targets are immobilized on the PEI-coated glass slides. The targets may include polynucleotides, oligonucleotides, haptens, cytokines, proteins, peptides, saccharides, and the like. The polynucleotides include nucleic acids in which the phosphodiester linkage has been replaced with a substitute linkage, such as phosphorothioate, methylimino, methylphosphonate, phosphoramidate, guanidine and the like;. nucleic acids in which the ribose subunit has been substituted, e.g. hexose phosphodiester; peptide nucleic acids, and the like. The polynucleotides may be single or double stranded, and may be PCR fragments amplified from cDNA. The polynucleotides may cover the known 5' or 3' nucleotide sequence, may be the full length sequence, or may be unique polynucleotides selected from particular areas along the length of the sequence. The polynucleotides used may be polynucleotides that are specific to a gene or genes of interest in which at least a fragment of the sequence is known, or that are specific to one or more unidentified cDNAs which are common to a particular cell type, developmental or disease state. The polynucleotides for use in the present invention may be synthetic polynucleotides or PCR fragments from about 2 to about 50,000 consecutive bases, preferably about 5 to about 500 consecutive bases in length, more preferably about 40–70 bases in length, most preferably about 50 to 65 bases in length. A spacer (linker) arm, i.e., a chemical moiety that extends or links other chemical groups, and preferably is a carbon chain containing from about 2 to about 12 carbon atoms, more preferably about 6 carbon atoms, containing a blocked amine group can be coupled during synthesis using conventional chemistry to the 5'-hydroxyl group of a polynucleotide. Alternatively, a polynucleotide can be modified at the 3'-end with a spacer arm containing a blocked amine group by methods well known in the art.

Preferably, a polynucleotide possessing a 5'-linker arm or a 3'-linker arm such as:

Eq.1 is employed wherein, as a spacer arm, n is 2–12 inclusive, preferably 6; Y is an amine or a thiol, preferably a primary amine; and A is an polynucleotide, ranging from between about 2–50000 consecutive bases, preferably about 5 to about 500 consecutive nucleotides, with only the 5'-hydroxyl or the 3'-hydroxy group requiring modification for attachment.

The selected polynucleotides are then associated with the polymer coated glass slides for manufacturing arrays and microarrays. The arrays may be produced according to any convenient methodology, and a number of different array configurations and methods for their production are known to those of skill in the art and disclosed in U.S. Pat. Nos.:5,445,934, 5,532,128; 5,384,261; and 5,700,637; the disclosure of which are herein incorporated in their entirety by reference. For example, the polynucleotides may be stably associated with the substrate through non-covalent means, such as by interacting with a positively charged surface of the substrate. Alternatively, the polynucleotides possessing the 5'- or the 3'-terminal linker arm may be bound to the substrate through covalent means, such as via an alkylamino-linker group. In another embodiment of the invention, the polynucleotides may be associated with the substrate through both non-covalent and covalent means.

In order to conduct sample analysis using the arrays and microarrays of the invention, the RNA or DNA from a biological sample is made into hybridization probes, as is well known in the art. The hybridization probes are then contacted with the arrays and microarrays of the invention under hybridization conditions to produce a hybridization pattern. Suitable hybridization conditions are well known to those of skill in the art and reviewed in WO 95/21944 to Maniatis et al. Incubation conditions are adjusted so that hybridization occurs with precise complementary matches or with various degrees of less complementarity. After removal of nonhybridized probes, a scanner is used for detection or visualization to determine the levels and patterns of fluorescence. A detection system may be used to measure the absence, presence, and amount of hybridization for all of the distinct sequences simultaneously.

The hybridization pattern can be used to determine quantitative information about the genetic profile of the nucleic acids in the sample that was contacted with the array to generate the hybridization pattern, as well as the physiological source from which the labeled sample nucleic acid was derived. The data provides information about the physiological source from which the sample nucleic acid were derived, such as the types of genes expressed in the tissue or cell which is the physiological source, as well as the levels of expression of each gene, particularly in quantitative terms.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperatures, etc.) but some experimental errors and deviations should be accounted for. Unless indicated otherwise, parts are parts by weight, molecular weight is weight average molecular weight, temperature is in degrees Centigrade, and pressure is at or near atmospheric.

The cDNA microarrays were made according to U.S. Pat. No. 5,807,522 to Brown et al. The polynucleotides were synthesized and purified by Operon Technologies, and used without further purification. The chemical reagents were obtained from Aldrich Chemical Company, and used without further purification. The organic solvents were of HPLC grade.

Example 1

This example serves to demonstrate a method of silylating a glass slide. Ten glass slides, visually inspected to be free of scratches, were selected. The selected glass slides were immersed in 1 L solution of 0.1% SDS in distilled water (w/v) and subjected to ultrasonication for approximately 30 minutes. The glass slides were then dried, treated to ultrasonication treatment in acetone for approximately 30 minutes, and air dried.

A 2.0% (w/v) silane solution was prepared by dissolving 3-aminopropyltrimethoxysilane in deionized water with gentle stirring. The dried glass slides were dipped in the silane solution for 2 minutes. The glass slides were rinsed free of excess silane solution by ultrasonication in distilled water for about two minutes, and rinsing with distilled water. The washed slides were cured at about 120° C. for about 30 minutes, and stored in a dustless environment until used.

Example 2

This example serves to demonstrate a method for making 60 PEI coated glass slides. All reactions were done at about 4° C. unless otherwise indicated. Cyanuric chloride (12.7 g) was dissolved in 1 L of n-hexane and sodium carbonate (25.0 g). Separately, polyethylenimine (1.0 g, MW 25,000 Da) was dissolved in 1 L distilled water at room temperature. The solutions, the glass slides from Example 1, 2 L of n-hexanes, and additional 1 L of distilled water were separately stored for at least 2 hours in a refrigerator capable of controlling the temperature at less than about 4° C. The glass slides were placed in two slide racks and the racks were place in the cyanuric chloride solution, with vigorous stirring of the solution. After about 1 hr., the glass slides were washed in 1 L of n-hexanes for about 10 minutes in an ultrasound cleaner, and air-dried. The slides were then placed in the polyethylenimine solution for about 1 hr. The slides were then washed with 1 L of distilled water for 10 minutes in an ultrasound cleaner, air dried, centrifuged to 1000 rpm, washed in 1 L of n-hexanes for about 10 minutes in an ultrasound cleaner, placed back in the cyanuric chloride solution for about 1 h., washed in 1 L of n-hexanes for about 10 minutes in an ultrasound cleaner, and air dried. The slides were then washed with about 1 L acetone for about 20 minutes in an ultrasound cleaner at room temperature twice, and air dried. The slides were then stored desiccated at about 2 to 25° C.

Example 3

This example serves to demonstrate a method for making 60 polylysine coated glass slides. The procedure of Example 2 was repeated, except 1 g of polylysine (Sigma) was used.

Example 4

This example serves to demonstrate a method for making 60 polyhistidine coated glass slides. The procedure of Example 2 was repeated, except 1 g of polyhistidine (Sigma) was used.

Example 5

The following example describes the application of polynucleotides onto a PEI-modified glass slide prepared in Example 2.

Figure 1:
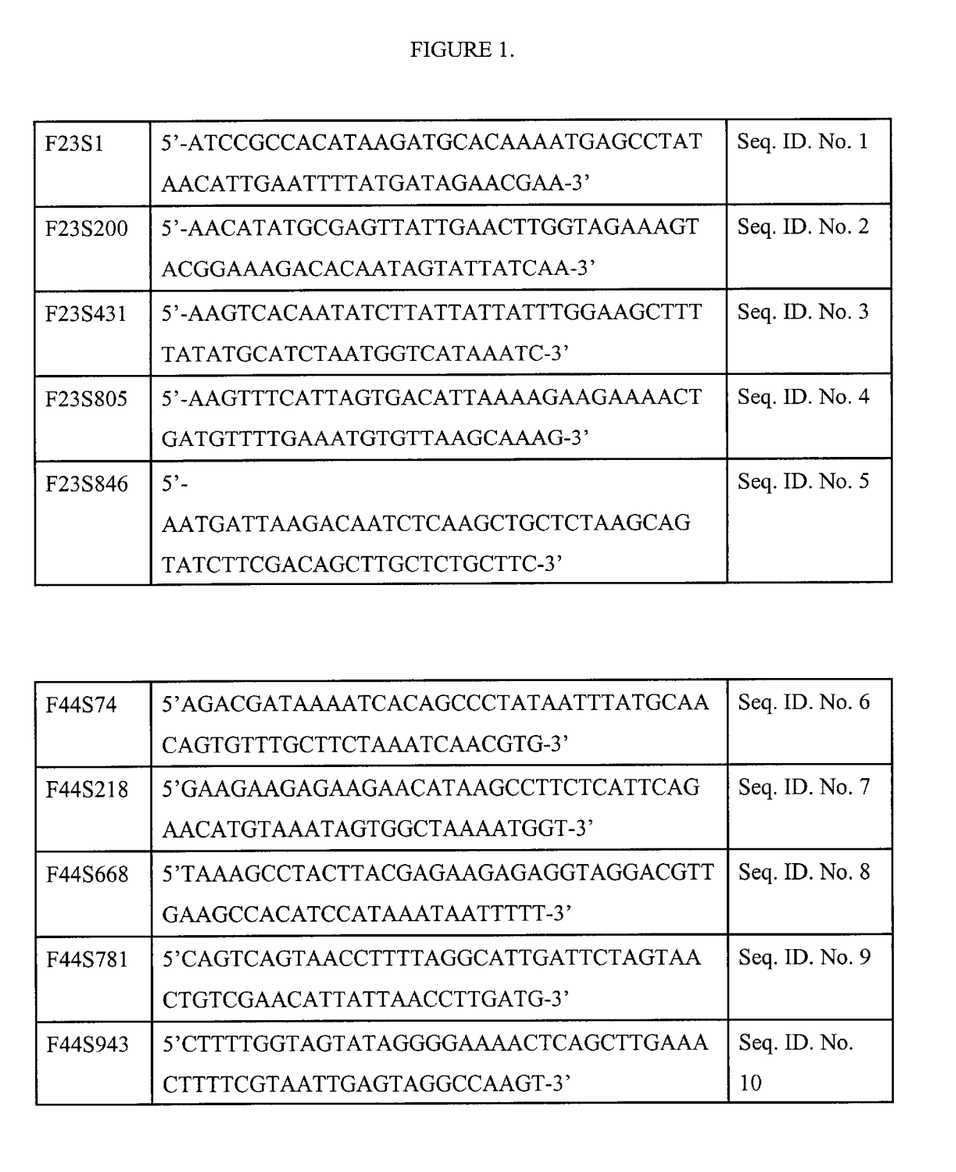
FIG. 1 provides a schematic representation of the five complimentary 59mer oligonucleotide of SEQ ID NO.: 1–5 to YCF 23 and the five complimentary oligonucleotide of SEQ ID NO.: 6–10 to YCF.44.

Synthetic oligodeoxyribonucleotides (59 bases in length with 3'-aminoalkyl linker modifications) were purchased from Operon Technologies(Alameda, Calif.). Seq. ID. No.: 1–5, shown in FIG. 1, each targeting a yeast control fragment (YCF 23) target sequence, were used in this experiment. Dilutions of these oligodeoxyribonucleotides (6.25–100 micromolar) were made in 2×SSC buffer (pH 7.4) and transferred to 96-well microtiter plates. The resulting samples were spotted onto polyethylenimine-modified glass slides in the Incyte Microarray Systems production facility. After arraying, the slides were washed in 0.2% SDS solution for 2 min. Next, the slides were rinsed in deionized water for 1 min. and immersed in a 2% casein solution in phosphate buffered saline at 60° C. for 30 min. Then, the slides were rinsed in 0.2% SDS for 5 min, rinsed in deionized water for 1 min, and spun dry.

Example 6

The following example describes the use of an array generated according to Example 5 in a hybridization experiment. A synthetic RNA transcript corresponding to the yeast control fragment (YCF 3) target sequence was prepared as follows. A clone containing the YCF 3 target sequence was provided by the Incyte Microarray Systems production facility. The clone was amplified with vector-specific primers to generate the corresponding PCR amplicon. This material was further amplified with PCR primers specific to the 3'- and 5'-ends of the target sequence. The forward primer contained a T7 promoter at its 3'-end (NNNNN NTAAT ACGAC TCACT ATAGG GAG) and the reverse primer contained a 30-base poly(dT) sequence at its 5'-end. The PCR products were purified using gel filtration. The purified T7 product was used as a template to generate RNA through in vitro transcription using Ambion's MEGAscribe á kit. (Austin, Tex.). The RNA was quantitated by UV spectroscopy.

Cy5-labeled cDNA probe was transcribed from 1 ng of RNA template by reverse transcription using 5' Cy5 labeled random 9-mers (Operon Technologies). Reactions were incubated for 2 hrs at 37° C. with 200 Units MMLV reverse transcriptase (Life Technologies, Gaithersburg, Md.), 4 mM DTT, 1 unit RNase Inhibitor (Ambion, Austin, Tex.), 0.5 mM dNTPs, and 2 mg of the Cy5-labeled random 9-mer in a buffer provided by the manufacturer (25 mL final volume). The reactions were terminated by incubation at 85° C. for 5 min. The reactions were then purified with a TE-30 column (Clontech, Palo Alto, Calif.), made upto a volume of 90 mL with deionized water, and precipitated with 2 mL 1 mg/mL glycogen, 60 mL 5M $NH_4OAc$, and 300 mL ethanol. The pellets were resuspended in 24 mL of hybridization solution: 5×SSC, 0.2% SDS, 1 mM DTT.

The Cy5-labeled cDNA probe was applied to the array, covered with a 22-$mm^2$ glass cover slip, placed in a sealed chamber to prevent evaporation, and incubated at 60° C. for six hrs. After the hybridization, the arrays were washed for 10 minutes in 1×SSC/0.1% SDS at 45° C. then for 3 minutes in 0.1×SSC/0.2% SDS at 25° C. The arrays were imaged by confocal laser scanning using GenePix™ scanners (Foster City, Calif.) with a 10 mm resolution. The signal was converted into 16-bits-per-pixel resolution, yielding a 65,536 count dynamic range. Incyte GEMtools™ software (Incyte Pharmaceuticals, Inc., Palo Alto, Calif.) was used for image analysis. Signals were corrected for local background. The example demonstrates the use of this invention for detection of a target sequence in a microarray format using immobilized polynucleotides.

Example 7

The following example compares the performance of glass slides coated with polyethlenimine, polylysine and polyhistidine.

Figure 2:
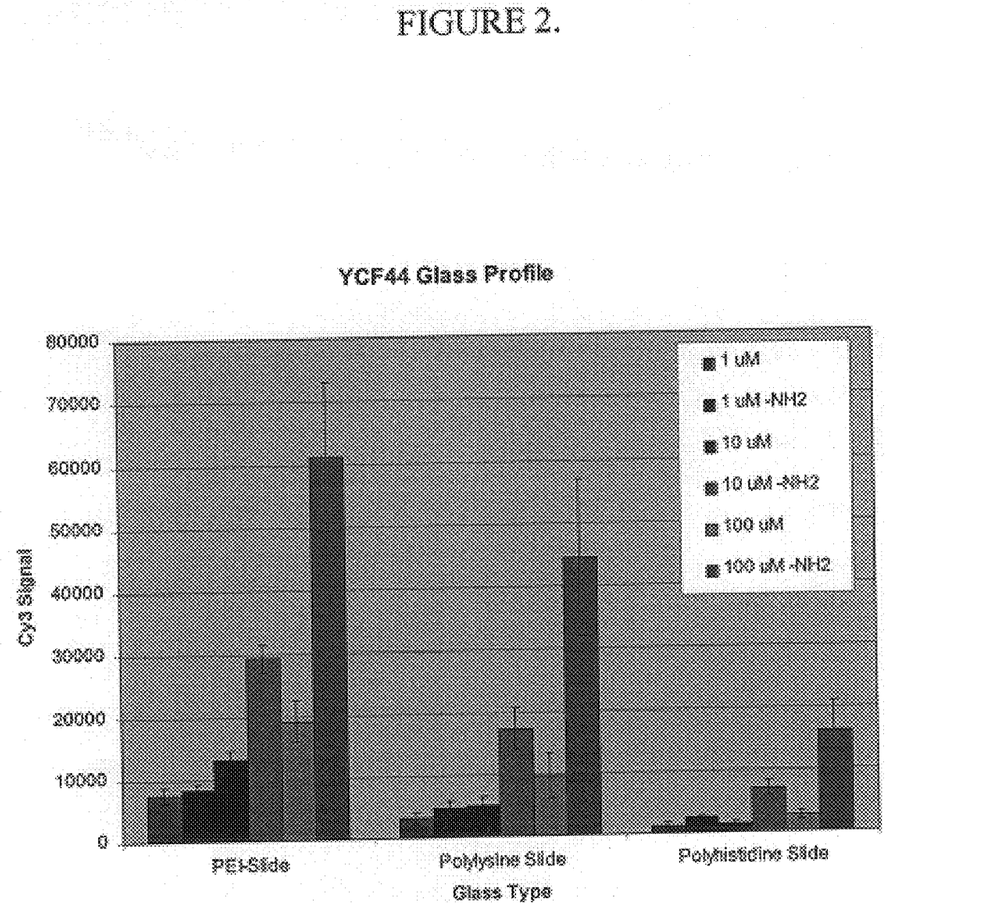
FIG. 2 illustrates the relative Cy3 signal intensities corresponding to the binding of the YCF 44 polynucleotides onto derivatized glass slides: polyethylenimine (PEI), polylysine or polyhistidine. In this analysis, the signals corresponding to each type of polynucleotide (with or without an aminolinker) at a given concentration were averaged.

In order to compare their ability to bind polynucleotides, and to examine the hybridization performance of the corresponding arrays, the following experiment was conducted. Polynucleotide sequences (Seq. ID. No.: 6–10, shown in FIG. 1) were designed against an intronic yeast control fragment sequence, YCF 44. The polynucleotides were purchased from Operon Technologies. Each sequence was synthesized as four different derivatives: (1) unmodified; (2) 3'- aminolinker modified (unlabeled); 5'-dye-labeled (cyanine 3, no aminolinker); and 5'-dye labeled (cyanine 3) plus 3'-aminolinker modified. Polynucleotides of the same sequence plus a 3'-aminolinker were mixed in a 10:90 molar ratio (dye labeled: unlabeled). Polynucleotides without a 3'-aminolinker were likewise mixed in a 10:90 molar ratio (dye labeled: unlabeled). Each mixture was reconstituted in 2×SSC buffer and distributed into a 96-well plate at 1 mM, 10 mM and 100 mM concentrations. Each of the resulting samples was then printed onto the modified glass substrates four times to enable signal averaging. Next, the slides were washed, blocked, and dried as described in Example 6. Then, the slides were scanned using a two-color laser-scanning device (Axon Instruments) to obtain a relative measure of the amount of Cy3 dye deposited at each spot. Representative data is shown in FIG. 2. In each case, the aminolinker-modified polynucleotides bound in greater abundance compared to the corresponding sequences without aminolinkers. Nevertheless, the data indicates that the polynucleotides bind via a mixture of covalent and noncovalent interactions.

Figure 3:
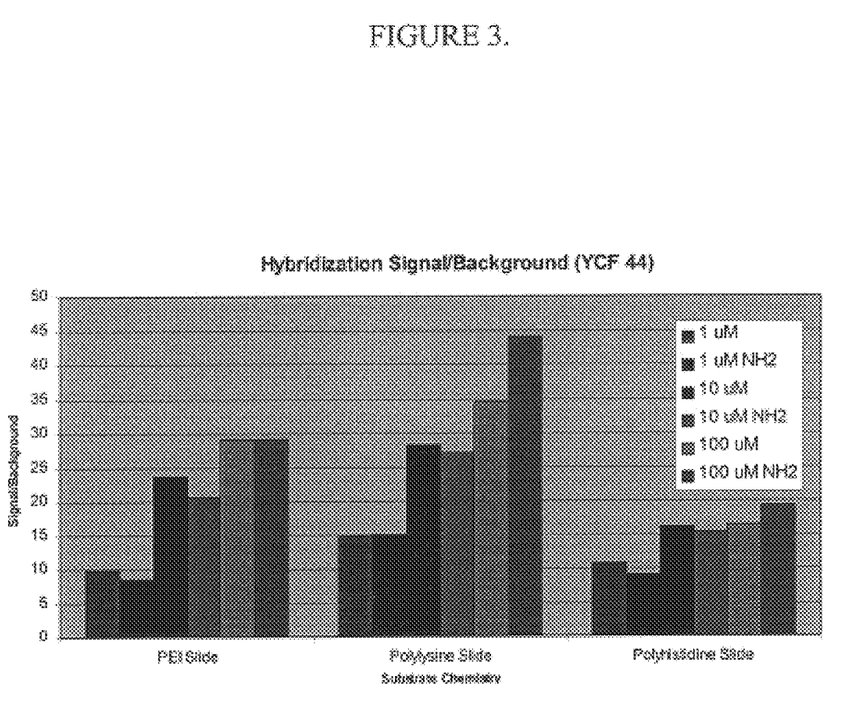
FIG. 3 illustrates the relative Cy5 signal intensities corresponding to the binding of polynucleotides onto derivatized glass slides: polyethylenimine (PEI), polylysine or polyhistidine. In this analysis, the signals corresponding to each type of polynucleotide (with or without an aminolinker) at a given concentration were averaged.

In order to measure the hybridization activity of polynucleotides bound onto the coatings according to this example, a synthetic RNA transcript was prepared from YCF 44 as described in the previous example. The generation of Cy5-labeled cDNA probe, hybridization and data analysis were conducted as described in the previous example. The resulting hybridized arrays were then scanned in the Cy5 channel to provide a relative measure of hybridized probe. Representative data is shown in FIG. 3.

What is claimed is:

1. A method of attaching target molecules to a surface of a solid support, the method comprising the ordered steps of:
   a) silylating the surface with an agent having the formula $H_2N-(CH_2)_n-SiX_3$ where n is between 1 and 10, and X is independently chosen from OMe, OEt, Cl, Br, or I,
   b) activating the surface with a first crosslinking reagent;
   c) reacting the surface with an amine-containing polymer to form a modified solid support surface; and
   d) attaching non-activated target molecules to the modified solid support surface, wherein the target molecules are arranged in a defined manner on the modified solid support surface thereby producing an array of attached target molecules.

2. The method of claim 1, wherein after the reacting step, the solid support surface is further modified with a second crosslinking reagent, and wherein target molecules are covalently attached to the modified solid support surface.

3. The method of claim 2, wherein the second crosslinking reagent is cyanuric chloride.

4. The method of claim 1, wherein the solid support surface is selected from the group consisting of glass, silica, plastic, ceramic, beads, and nylon, and combinations thereof.

5. The method of claim 1, wherein the solid support surface is glass.

6. The method of claim 1, wherein the crosslinking reagent is cyanuric chloride.

7. The method of claim 1, wherein the amine-containing polymer is selected from the group consisting of polyethylenimine, polyhistidine, polylysine, and polyarginine, and combinations thereof.

8. The method of claim 1, wherein the amine-containing polymer is polyethylenimine.

9. The method of claim 1, wherein the target molecules are selected from the group consisting of target polynucleotides, target polypeptides and target polysaccharides.

10. The method of claim 1, wherein the target molecules are target polypeptides.

11. The method of claim 1, wherein the target molecules are target polypeptides, the solid support surface is glass, the crosslinking reagent is cyanuric chloride, and the amine-containing polymer is polyethylenimine.

12. The method of claim 1, wherein the target molecules are target antibodies.

13. The method of claim 1, wherein the target molecules are target antibodies, the solid support surface is glass, the crosslinking reagent is cyanuric chloride, and the amine-containing polymer is polyethylenimine.

14. The method of claim 1, wherein the target molecules are target monoclonal antibodies.

15. The method of claim 1, wherein the target molecules are target monoclonal antibodies, the solid support surface is glass, the crosslinking reagent is cyanuric chloride, and the amine-containing polymer is polyethylenimine.

16. The method of claim 1, wherein the target molecules are not covalently attached to the modified solid support surface.

17. The method of claim 1, wherein the target molecules are not covalently attached to the modified solid support surface, the solid support surface is a glass slide, and the attaching step produces a microarray of the target molecules on the slide.

18. An array of attached target molecules, the array made by the method of claim 1.

19. The array of claim 18, wherein after the reacting step, the solid support surface is further modified with a second crosslinking reagent, and wherein target molecules are covalently attached to the modified solid support surface.

20. The array of claim 19, wherein the second crosslinking reagent is cyanuric chloride.

21. The array of claim 18, wherein the solid support surface is selected from the group consisting of glass, silica, plastic, ceramic, beads, and nylon, and combinations thereof.

22. The array of claim 18, wherein the solid support surface is glass.

23. The array of claim 18, wherein the crosslinking reagent is cyanuric chloride.

24. The array of claim 18, wherein the amine-containing polymer is selected from the group consisting of polyethylenimine, polyhistidine, polylysine, and polyarginine, and combinations thereof.

25. The array of claim 18, wherein the amine-containing polymer is polyethylenimine.

26. The array of claim 18, wherein the target molecules are selected from the group consisting of target polynucleotides, target polypeptides and target polysaccharides.

27. The array of claim 18, wherein the target molecules are target polypeptides.

28. The array of claim 18, wherein the target molecules are target polypeptides, the solid support surface is glass, the crosslinking reagent is cyanuric chloride, and the amine-containing polymer is polyethylenimine.

29. The array of claim 18, wherein the target molecules are target antibodies.

30. The array of claim 18, wherein the target molecules are target antibodies, the solid support surface is glass, the crosslinking reagent is cyanuric chloride, and the amine-containing polymer is polyethylenimine.

31. The array of claim 18, wherein the target molecules are target monoclonal antibodies.

32. The array of claim 18, wherein the target molecules are target monoclonal antibodies, the solid support surface is glass, the crosslinking reagent is cyanuric chloride, and the amine-containing polymer is polyethylenimine.

33. The array of claim 18, wherein the target molecules are not covalently attached to the modified solid support surface.

34. The array of claim 18, wherein the target molecules are not covalently attached to the modified solid support surface, the solid support surface is a glass slide, and the attaching step produces a microarray, of the target molecules on the slide.

* * * * *